(12) United States Patent
Hargrave et al.

(10) Patent No.: US 7,591,798 B2
(45) Date of Patent: Sep. 22, 2009

(54) ANKLE BRACE

(75) Inventors: David C. Hargrave, Madison, NJ (US); Fabian McCarthy, Jr., Basking Ridge, NJ (US)

(73) Assignee: DJO, LLC, Vista, CA (US)

( * ) Notice: Subject to any disclaimer, the term of this patent is extended or adjusted under 35 U.S.C. 154(b) by 487 days.

(21) Appl. No.: 11/140,166

(22) Filed: May 27, 2005

(65) Prior Publication Data

US 2006/0004311 A1  Jan. 5, 2006

Related U.S. Application Data

(60) Provisional application No. 60/575,038, filed on May 27, 2004, provisional application No. 60/655,500, filed on Feb. 22, 2005.

(51) Int. Cl.
 *A61F 5/00* (2006.01)
(52) U.S. Cl. ......................................... 602/23; 602/27
(58) Field of Classification Search ................ 602/5, 602/6, 13, 23, 27; 128/882, DIG. 20
See application file for complete search history.

(56) References Cited

U.S. PATENT DOCUMENTS

| | | | |
|---|---|---|---|
| 4,187,844 A | 2/1980 | Caprio, Jr. | |
| 4,495,942 A | 1/1985 | Palumbo | |
| 4,727,863 A | 3/1988 | Nelson | |
| 5,520,628 A | 5/1996 | Wehr | |
| 5,620,413 A | 4/1997 | Olson | |
| 5,621,985 A | 4/1997 | Frost | |
| 5,665,059 A | 9/1997 | Klearman et al. | |
| 5,833,639 A * | 11/1998 | Nunes et al. | .................. 602/23 |
| 5,891,073 A | 4/1999 | Deirmendjian et al. | |
| 5,954,075 A | 9/1999 | Gilmour et al. | |
| 6,117,098 A | 9/2000 | Weber et al. | |
| 6,394,971 B1 * | 5/2002 | Slautterback et al. | ......... 602/27 |
| 6,503,218 B1 | 1/2003 | Ascheman | |
| 6,656,145 B1 | 12/2003 | Morton | |
| 6,663,583 B1 * | 12/2003 | Janis | .......................... 602/65 |
| 6,871,424 B2 * | 3/2005 | Labonte et al. | ............... 36/115 |
| 2001/0031936 A1 | 10/2001 | Pior et al. | |
| 2004/0082895 A1 | 4/2004 | Price et al. | |

FOREIGN PATENT DOCUMENTS

| | | |
|---|---|---|
| DE | 2626479 | 12/1977 |
| DE | 8603420 | 4/1986 |
| EP | 0297026 | 12/1988 |

\* cited by examiner

*Primary Examiner*—Michael A. Brown
(74) *Attorney, Agent, or Firm*—Ropes & Gray LLP

(57) ABSTRACT

A brace worn by a user has side shell portions disposed in or on the lateral and medial sides portions of the brace to support the medial and lateral sides of the user's ankle. The shell may include a connecting center portion that extends under the foot of the user and couples the medial and lateral side shell portions. In certain embodiments, the connecting portion includes a plurality of flexible fingers oriented substantially towards the user's toes for yielding to the movement of the user's foot while maintaining the stability and orientation of the lateral and medial supports with respect to the user's ankle.

28 Claims, 7 Drawing Sheets

ANKLE BRACE

CROSS REFERENCE TO RELATED APPLICATIONS

This claims the benefit of U.S. Provisional Patent Application No. 60/575,038, filed May 27, 2004, and U.S. Provisional Patent Application No. 60/655,500, filed Feb. 22, 2005, each of which is hereby incorporated by reference herein in its entirety.

BACKGROUND OF THE INVENTION

The systems and methods described herein relate generally to orthopedic devices and, more particularly, to ankle braces for stabilizing the ankle against inversion and eversion without limiting normal plantarflexion and dorsiflexion of the ankle.

Certain injuries to the lower extremities, including the ankle, are remarkably common. Such injuries may include severe ankle sprains. Once injured, the extremity often becomes unstable for some period of time, and the risk of re-injury is high. Moreover, repetitive sprains occurring over several years can result in long-term weakness.

Thus, it is desirable to have a brace that allows the user to move freely, while at the same time providing support during the recuperation period and providing long-term support to reduce the chance for re-injury.

There are a number of known ways to stiffen fabric orthopedic supports for injured parts of the anatomy. U.S. Pat. No. 4,724,847, for example, discloses an ankle brace that has a plurality of pockets. Rigid stay members are inserted into the pockets to form a rigid structure that surrounds and immobilizes the ankle. U.S. Pat. Nos. 3,298,365, 4,280,488, 4,440,158, and 4,825,856, among others, disclose similar arrangements.

A drawback of these designs is that multiple stays are typically formed and inserted independently into the pockets of the brace and are therefore not able to sufficiently maintain a particular orientation with respect to the ankle during plantarflexion and dorsiflexion. Furthermore, the stays are typically die-cut from plastic of constant thickness and secured within the pockets during manufacture. The shape of the stays is therefore quite limited, and the final support often does not fit the anatomy adequately.

Accordingly, it would be advantageous to be able to provide a brace that stabilizes the ankle against inversion and eversion without limiting normal plantarflexion and dorsiflexion thereof.

SUMMARY OF THE INVENTION

It is an object of this invention to provide a brace that stabilizes the ankle against inversion and eversion without limiting normal plantarflexion and dorsiflexion thereof.

The brace described herein is capable of stabilizing the ankle against eversion and inversion, while permitting dorsiflexion and plantarflexion, and while being worn inside a conventional shoe, sneaker, boot, or other footwear. In certain embodiments, ambulatory functionality and permitted exercises are feasible, thereby assisting recovery from various injuries to the lower extremity, such as ankle sprains. Additionally, the brace can function to replace athletic adhesive tape of the type commonly employed to support an ankle and prevent injury or re-injury.

In accordance with the systems and methods described herein, there is provided a brace for supporting a user's ankle. The brace includes a boot assembly and a shell member. The boot assembly has a medial side boot portion dimensioned and configured to extend along a medial side of the user's leg and foot, a lateral side boot portion dimensioned and configured to extend along a lateral side of the user's leg and foot, and a base boot portion connecting said side boot portions under the user's foot. The shell member has at least one side shell portion disposed in or on at least one of the medial and lateral side boot portions of the boot assembly for providing support to at least one of the medial and lateral sides of the user's ankle. The shell member also has a center shell portion coupled to the at least one side shell portion. The center shell portion is positioned under the user's forefoot and has a plurality of fingers oriented substantially towards the user's toes. The fingers of the center shell portion yield to movement of the user's forefoot for providing stability to the at least one side shell portion.

BRIEF DESCRIPTION OF THE DRAWINGS

The above and other advantages of the invention will be more apparent upon consideration of the following detailed description, taken in conjunction with the accompanying drawings, in which like reference characters refer to like parts throughout, and in which.

DETAILED DESCRIPTION OF THE INVENTION

Figure 1:
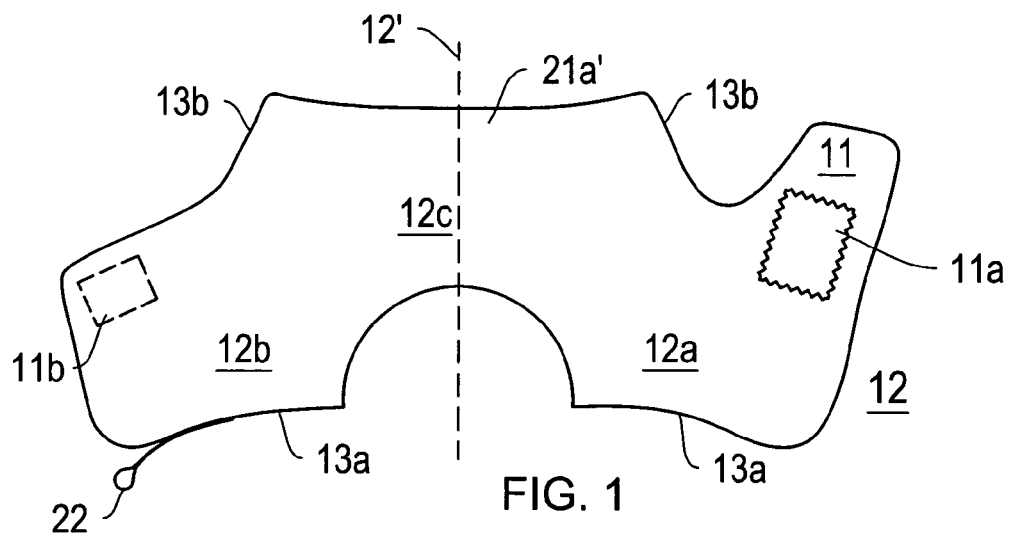
FIG. 1 is a planar view of the structure of a boot assembly according to the invention.

The systems and methods described herein provide a brace that stabilizes the ankle of a user against inversion and eversion without limiting normal plantarflexion and dorsiflexion thereof. More particularly, a soft ankle brace disclosed herein may be made of a pliable material formed as a boot that can be fitted over a user's appendage, such as the ankle. Disposed within or adjacent to the boot is a pliable but resilient shell that provides support to the medial and lateral sides of the user's ankle. The shell may include a connecting center portion that extends under the foot of the user and couples between the lateral support and the medial support. In certain embodiments, the connecting portion includes a plurality of flexible fingers oriented substantially towards the user's toes for yielding to the movement of the user's foot while maintaining the stability and orientation of the lateral and medial supports with respect to the user's ankle.

The brace further includes at least one strap that winds upwardly from the forefoot of the boot to the upper section of the boot where it may be wrapped once, or a plurality of times, around the upper portion of the boot. In certain embodiments, the brace also includes a vertically extending strap that is movable and that optionally may be inclined between 50° and 85° from the plane defined by the patient's foot.

The invention will now be described with reference to FIGS. 1-13.

FIGS. 1-13 illustrate an exemplary embodiment of a brace 10 for stabilizing a user's ankle. Brace 10 includes a body (or boot assembly) 12 and a support structure 14. Structure 14 includes a long strap 16, a vertical strap 18, strap loops 19, and a D-ring 20. Assembly 12 and structure 14 may be joined to form a pocket 15 therebetween that is adapted to receive a support shell 30.

Figure 2:
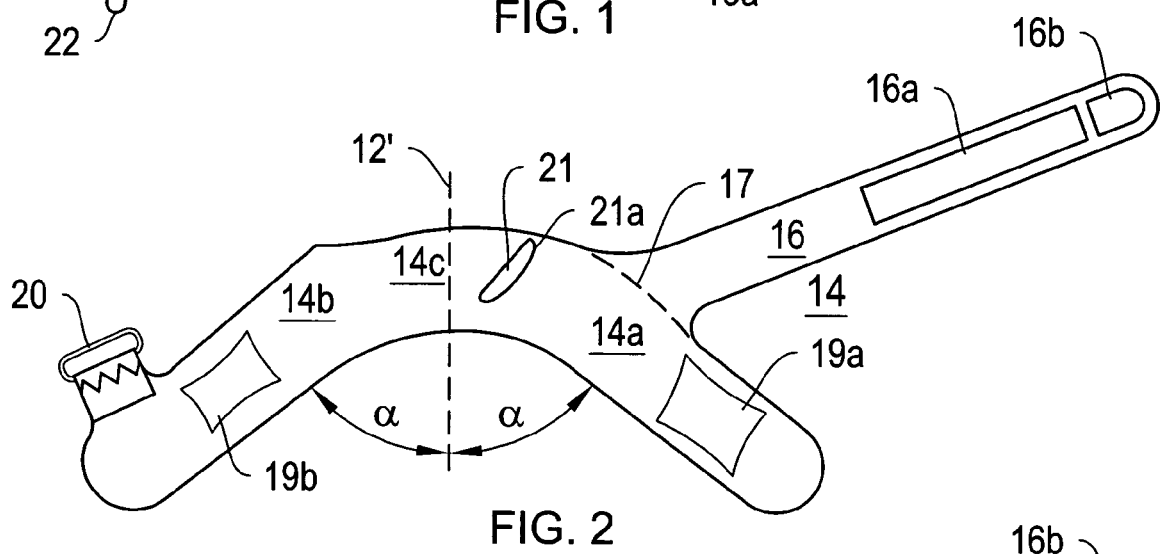
FIG. 2 is a planar view of a support structure according to the invention.
Figure 3:
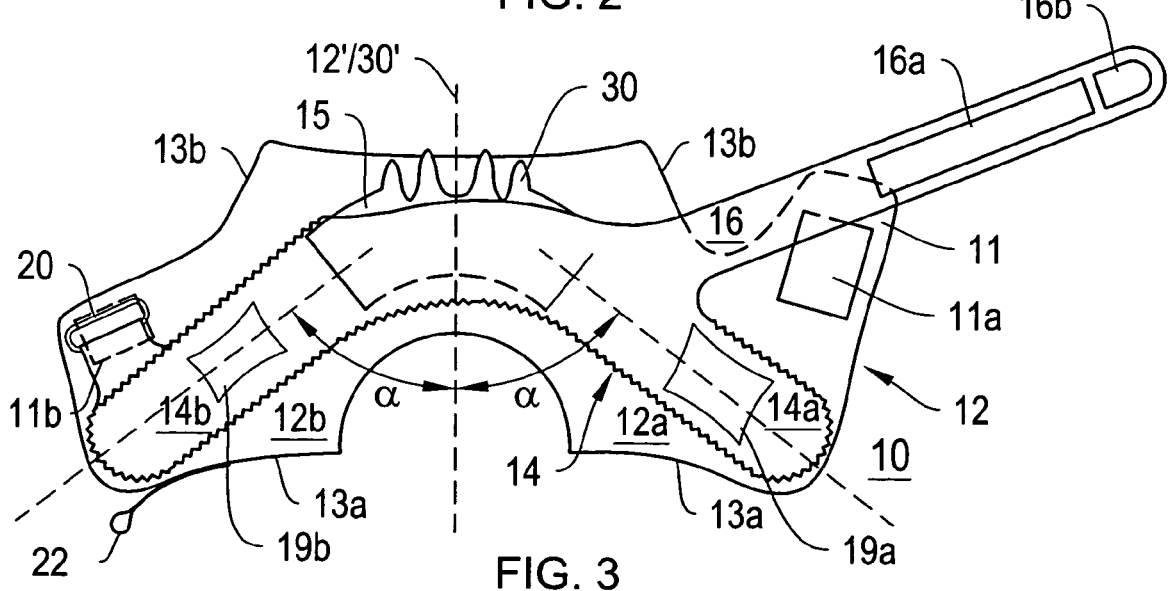
FIG. 3 is a planar view of a brace according to the invention incorporating the boot assembly of FIG. 1 and the support structure of FIG. 2.

FIGS. 1 and 3 show a planar view of an integral, one-piece (unitary), foot-shaped boot assembly 12. In particular, the left and right heel edges 13a of the structure shown in FIGS. 1 and 3 are joined to and integral with one another. Moreover, the left and right forefoot edges 13b of the structure shown in FIGS. 1 and 3 are joined to and integral with one another. Thus, the actual structure of boot assembly 12 is as shown in FIGS. 4-10, although FIGS. 1 and 3 are useful to more clearly reveal certain details of various features of brace 10. A central longitudinal axis 12', about which boot assembly 12 is formed, is shown in FIGS. 1-3 and 10. It is to be understood, that while each pair of edges 13a and edges 13b is described and shown as being integral in the depicted embodiment, each pair of edges 13a and edges 13b may be coupled to one another in many other suitable ways. For example, edges 13a may be snapped together by the user while edges 13b may be joined by a hook and loop arrangement (e.g., using Velcro™).

Boot assembly 12 may include a medial side portion 12a dimensioned and configured to extend along a medial side of a user's leg and foot, a lateral side portion 12b dimensioned and configured to extend along a lateral side of a user's leg and foot, and a base portion 12c coupling side portions 12a and 12b. Assembly 12 may also include a front flap portion 11 extending from medial side portion 12a, for example. In certain embodiments, front flap portion 11 may include a securing element 11a that is configured to interact with a corresponding securing element 11b provided elsewhere on assembly 12 to secure front flap portion 11 about the front of a user's leg, as is described in more detail below with respect to FIGS. 4-10. Securing elements 11a and 11b may be provided as a strip of minute hooks and a corresponding strip of uncut pile (i.e., Velcro™), or any other type of adjustable adhesive that allows a user to selectively alter the tightness of boot assembly 12 about his or her leg. For example, in certain embodiments, elements 11a and 11b may be provided as a configuration of running lace and lace apertures.

A suitable material for boot assembly 12 is nylon-coated neoprene. Other examples of suitable materials are nylon, neoprene, cotton, plastic, foam, canvas, rubber, spandex, or any other breathable, elastic, non-elastic, or suitable combination thereof that may be configured to support a user's ankle. It should be noted that, depending on the material of the assembly, different techniques may be used to shape the structure of boot assembly 12 shown in FIGS. 1 and 3 into approximately the fully shaped geometry of FIGS. 4-10 that boot assembly 12 may assume.

FIG. 2 shows a shell support structure 14 that may be disposed in or on boot assembly 12. In particular, structure 14 may be disposed on assembly 12 as shown in FIG. 3 to form brace 10 and may include at least one side pocket portion (e.g., medial side pocket portion 14a and/or lateral side pocket portion 14b) to form at least one side pocket on brace 10 that is adapted to receive a side portion of a support shell 30 (described in more detail hereinbelow). In certain embodiments, structure 14 includes both side pocket portions 14a and 14b, and a connecting base portion 14c therebetween.

A suitable material for structure 14 is nylon. Other examples of suitable materials are mesh, cotton, canvas, or any suitable combination thereof that may be configured to receive a support shell 30 in the space provided between structure 14 and assembly 12.

As shown in FIG. 2, structure 14 may also include a long strap 16, extending from a strap attachment location 17 at the union of base portion 14c and one of side portions 14a or 14b, a D-ring 20 coupled to the end of the other one of side portions 14a or 14b, for example, and strap loops 19a and 19b located on respective side portions 14a and 14b. In certain embodiments, the tip of strap 16 may include a securing element 16b that is configured to interact with a corresponding securing element 16a provided elsewhere on strap 16 to secure brace 10 about the user's ankle in conjunction with loops 19 and D-ring 20, as will be described in more detail hereinbelow with respect to FIGS. 4-10. Like elements 11a and 11b, securing elements 16a and 16b may be provided as a strip of minute hooks and a corresponding strip of uncut pile (i.e., Velcro™), or as any other type of adjustable adhesive that allows a user to selectively alter the tightness of strap 16 about his or her ankle. For example, in an alternative embodiment, elements 16a and 16b may be provided as snap-buttons or the like. Strap 16 is integral with structure 14, but in other embodiments strap 16 may be coupled to brace 10 in any suitable fashion.

FIGS. 3-10 show how boot assembly 12 of FIG. 1 and support structure 14 of FIG. 2 may be combined to form brace 10. In certain embodiments, support structure 14 and assembly 12 create a pocket 15 therebetween that is adapted to receive a support shell 30 (described in more detail hereinbelow). In certain embodiments, structure 14 is sewn to boot assembly 12 to form pocket 15, however any suitable means may be used to couple structure 14 to assembly 12 for forming pocket 15.

Figure 4:
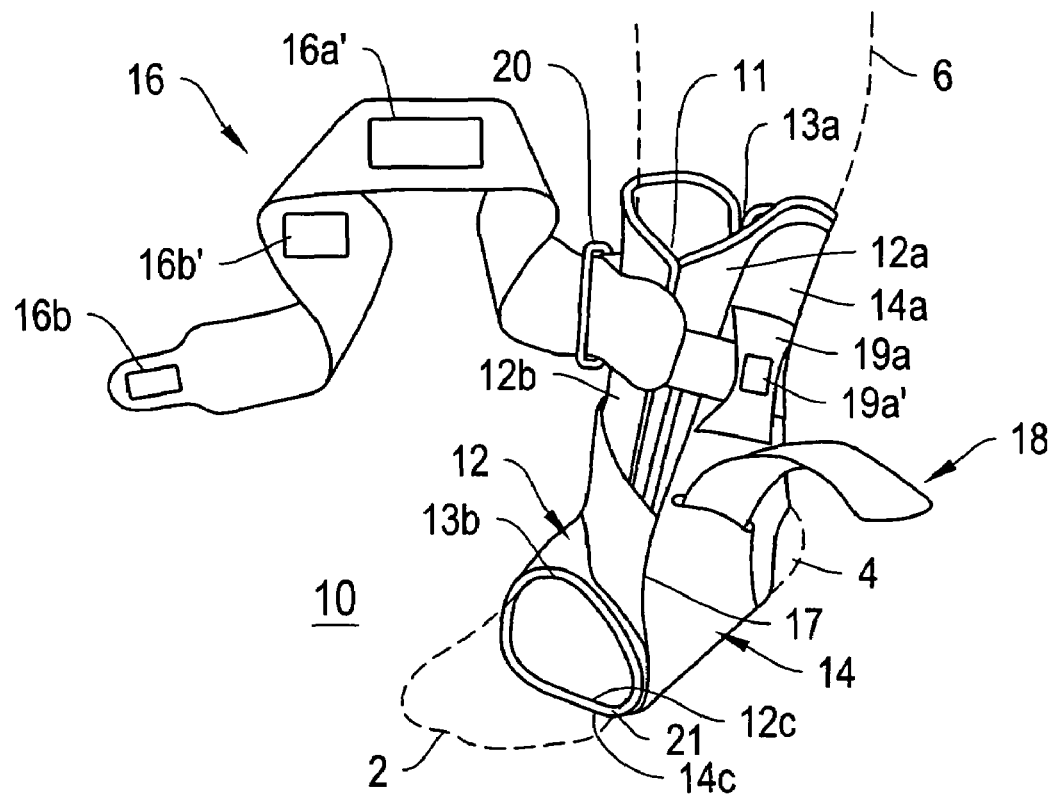
FIGS. 4-8 are perspective views of the brace of FIG. 3 in various stages of use.
Figure 5:
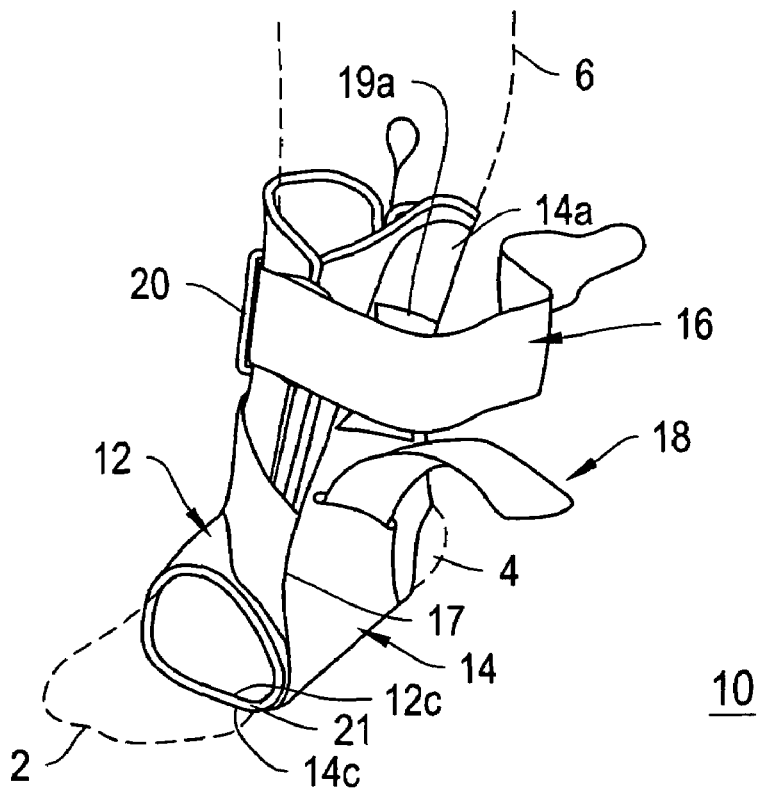
Figure 6:
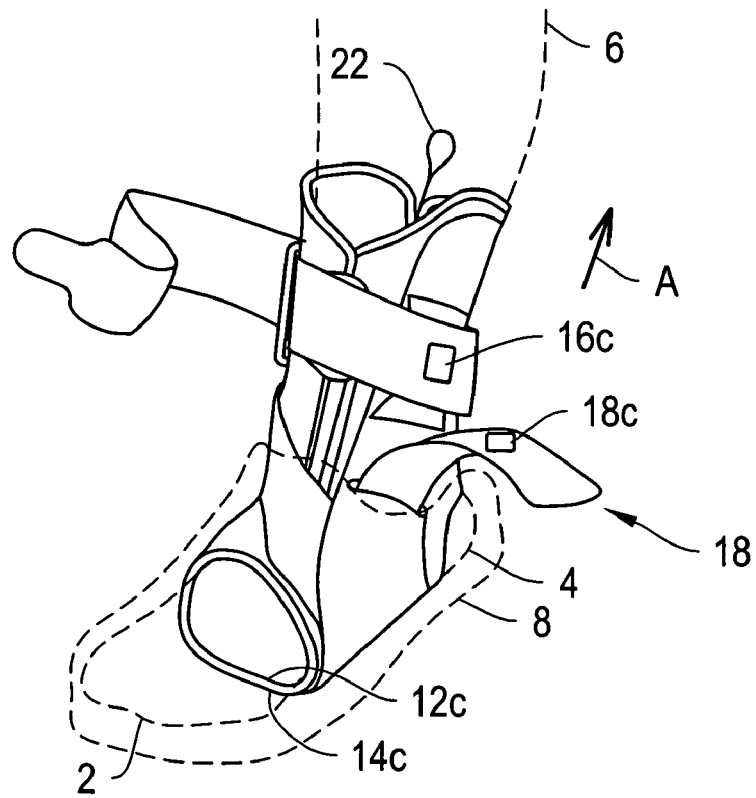
Figure 7:
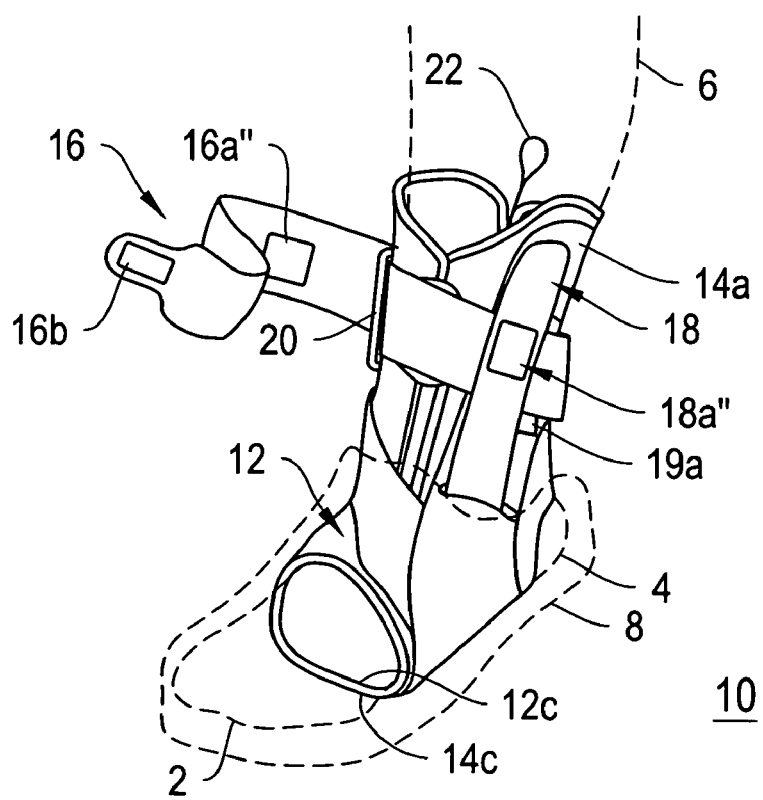

FIGS. 4-6 depict the wrapping of brace 10 around a patient's ankle (i.e., toes 2, heel 4, and leg 6 of a user, as shown in broken line) according to one embodiment of the invention. Specifically, FIG. 4 shows that, once body 12 is fitted around the patient's ankle and element 11a interacts with 11b (not shown) to secure front flap portion 11, long strap 16 can be fed from its strap attachment 17 at the user's forefoot between toes 2 and heel 4, through loop 19b (see, e.g., FIG. 9), around the back of the user's heel, through loop 19a, through D-ring 20, and pulled tightly so that attachment 17 is pulled tightly and the forefoot of the user is held securely within a plane that includes axis 12' (see, e.g., FIG. 10). The user can then begin wrapping strap 16 about the upper end of brace 10.

Turning to FIG. 5, it is shown that long strap 16 can be fed back about D-ring 20 and pulled around the upper portion of brace 10, thereby positioning strap 16 between brace 10 and an optional vertical strap 18. In certain embodiments, there may be securing elements provided on the external side of loop 19a (see, e.g., securing element 19a' shown in FIG. 4) and the portion of long strap 16 that crosses the external side of loop 19 (see, e.g., portion 16a' of securing element 16a shown in FIG. 4) such that long strap 16 may be secured in the position shown in FIG. 5 to hold the upper portion of brace 10 about leg 6 with a desired tightness.

In certain embodiments, a vertical strap 18 may be provided at an attachment location 21 on structure 14 (see, e.g., FIG. 2) to tighten the fit between a user's foot and base portions 12c and 14c of brace 10, as will be described in more detail hereinbelow. In an alternative embodiment, structure 14 may include a slot 21a at the location of depicted attachment 21 in FIG. 2. Slot 21a in structure 14 allows vertical strap 18 to enter the inner section of brace 10 and attach directly, or adjacent, at location 21a' (see, e.g., FIG. 1) to the material of base portion 12c of assembly 12, which fits against the bottom of the user's forefoot.

As shown in FIG. 6, a shoe or any suitable footwear 8 may be put on the user's foot about brace 10. A user may then pull upwardly in the direction of arrow A on a strap 22 provided on the top of assembly 12 to adjust the position of brace 10 on his or her ankle once footwear 8 has been fitted. Vertical strap 18 can also be pulled upwardly in the direction of arrow A, thereby again securing the patient's foot in a desired position with respect to brace 10. In certain embodiments, there are securing elements provided on one side of long strap 16 (see, e.g., securing element 16c shown in FIG. 6) and the portion of vertical strap 18 that crosses the side of long strap 16 (see, e.g., securing element 18c shown in FIG. 6) such that vertical strap 18 may be secured in the position shown in FIG. 7, thereby holding the lower portion of brace 10 (i.e., base portions 12c and 14c) underneath and against the portion of the user's forefoot between toes 2 and ankle 4 with a desired tightness.

Figure 8:
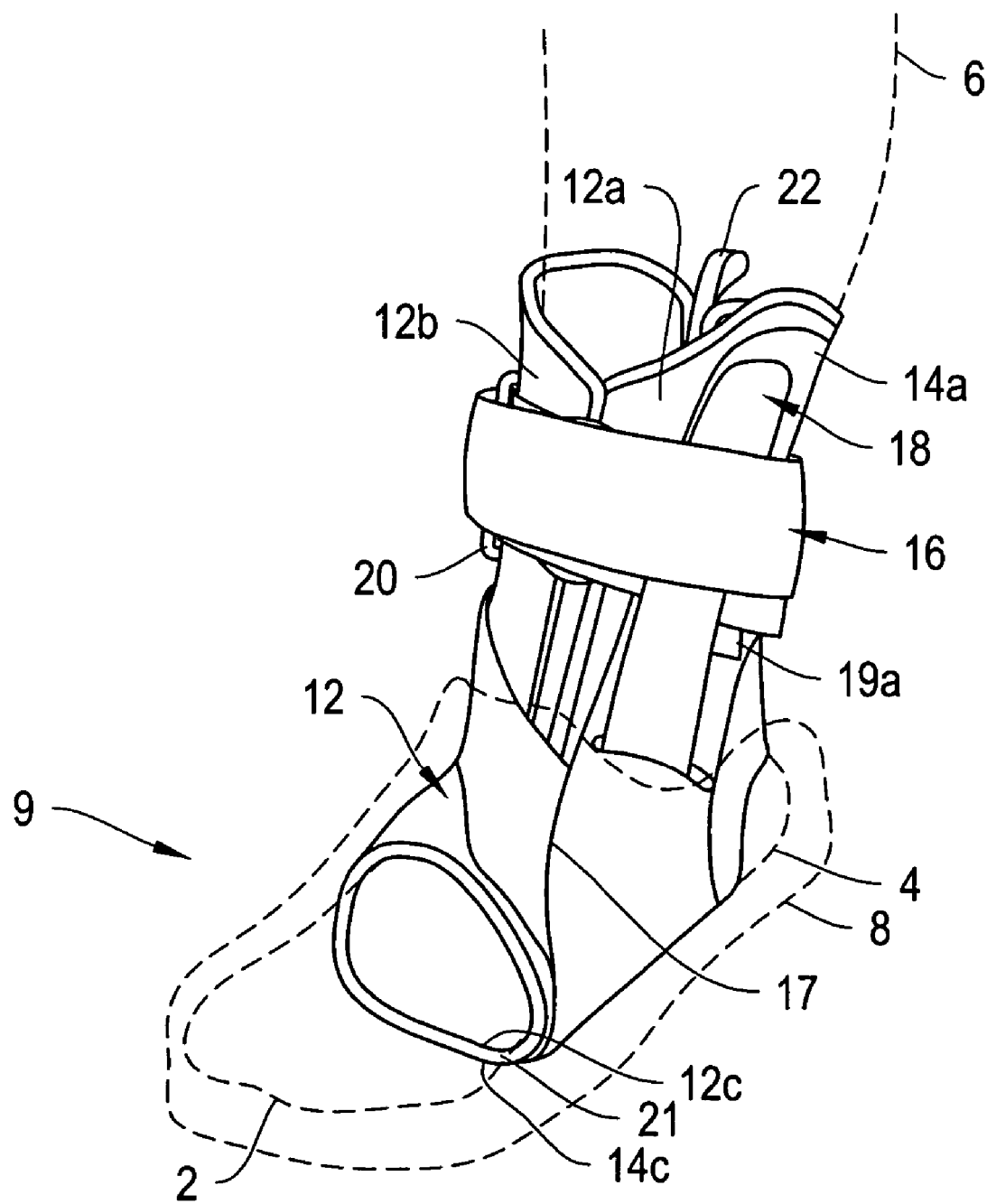
Figure 9:
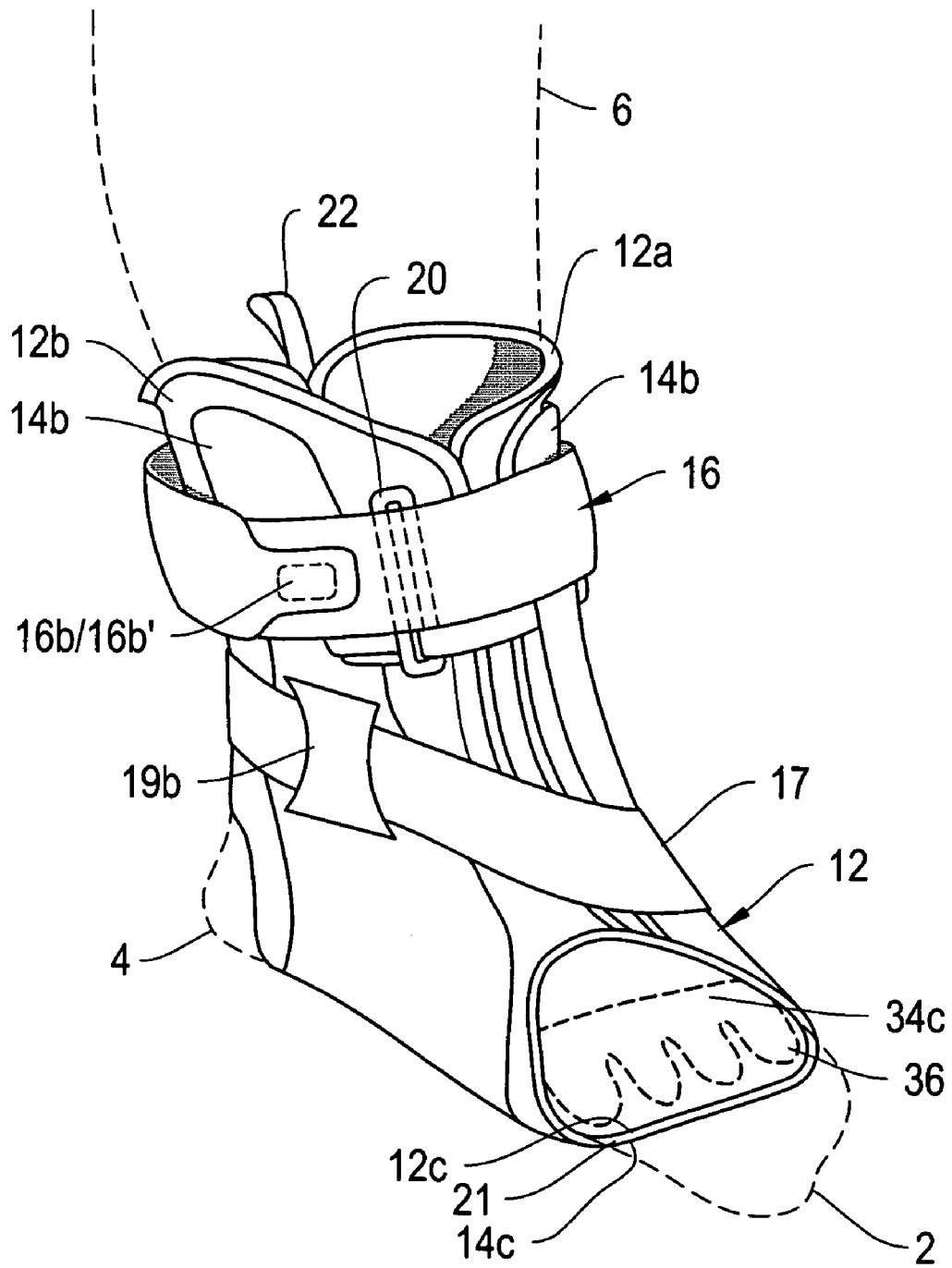
FIG. 9 is a perspective view of the brace of FIGS. 3-8, taken from line 9-9 of FIG. 8.
Figure 10:
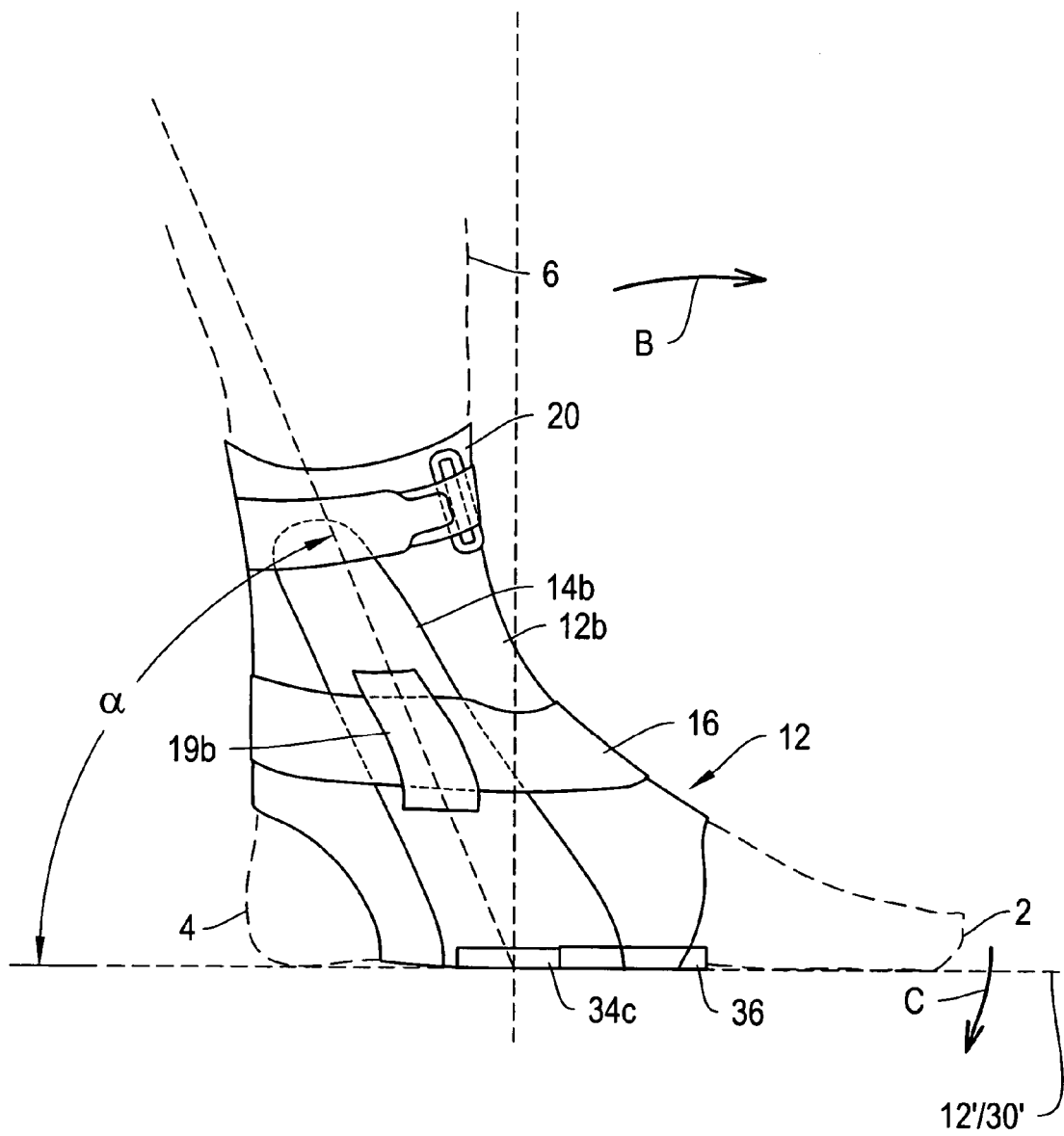
FIG. 10 is a side view of the brace of FIGS. 3-9.

Finally, as depicted in FIGS. 8-10, long strap 16 may then be wound about the exterior of vertical strap 18, thereby locking straps 16 and 18, and therefore the forefoot and ankle of the user, in the desired position with respect to the overall structure of brace 10. In certain embodiments, there are securing elements provided on one side of long strap 16 (see, e.g., portion 16a" of securing element 16a shown in FIG. 7) and the portion of vertical strap 18 that crosses the side of long strap 16 (see, e.g., securing element 18a" shown in FIG. 7) such that vertical strap 18 may be secured in the position shown in FIGS. 8-10. Furthermore, there may be securing elements provided at the tip of one side of long strap 16 (see, e.g., securing element 16b shown in FIGS. 2-4 and 7) and on the other side of long strap 16 (see, e.g., securing element 16b' shown in FIG. 4) such that long strap 16 may be secured in the position shown in FIGS. 8-10.

As mentioned above, and as shown in FIG. 3, brace 10 may further include a shell 30 that provides medial and lateral side support and mechanical stiffness to brace 10. In certain embodiments, shell 30, or portions thereof, is pliable and can be made of any suitable material, such as polyethylene, polypropylene, metal, composite, or any combination thereof. Shell 30 may be disposed within brace 10, for example, in pocket 15, as indicated in FIG. 3. The shell may be coupled to brace 10 by inserting it into pocket 15, which is formed by the space between assembly 12 and structure 14 (see, e.g., FIG. 3). However, instead of forming pockets on assembly 12, shell 30 may be fitted directly on the outside of boot assembly 12 with Velcro™, snaps, and/or any other conventional attachment means, or shell 30 can be an integral part of the outside of boot assembly 12 using injection molding, for example, thereby obviating the need for pocket 15 and, thus, side pocket portions 14a and 14b. Alternatively, the material of assembly 12 itself may be provided with pockets, slits, or the like into which the shell may be inserted and which will removeably hold shell 30 in place on brace 10.

In any case, shell 30 is provided to lend support to the user's ankle and to give stiffness and biomechanical stability to brace 10. The actual configuration employed for disposing shell 30 in or on brace 10 can vary according to the application, and any suitable configuration may be employed without departing from the spirit and scope of the invention. In certain embodiments, shell 30 is removable or changeable to let the user select shells of different sniffinesses, lengths, and angles with respect to the user's forefoot, as will be described in more detail hereinbelow.

Figure 11:
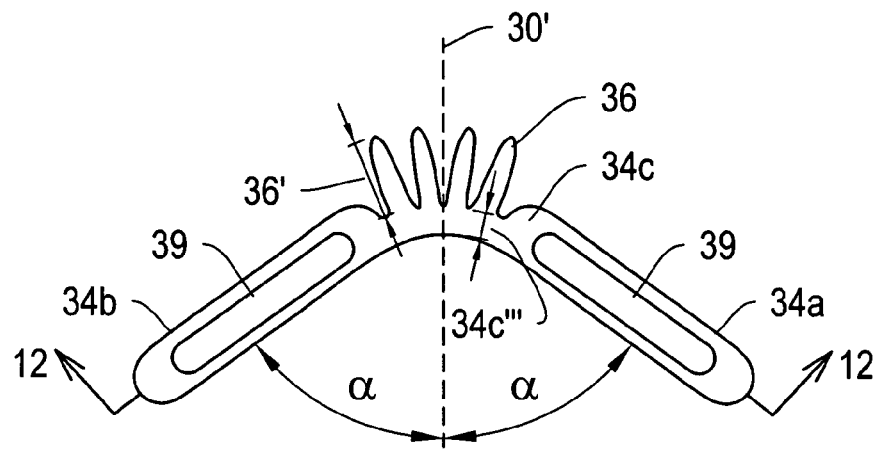
FIG. 11 is a planar development of the structure of a support shell according to the invention.

FIG. 11 shows an exemplary embodiment of shell 30 in accordance with the invention that may include at least one side shell support portion (e.g., medial side shell portion 34a and/or lateral side shell portion 34b). In certain embodiments, shell 30 includes both side shell portions 34a and 34b, and a connecting center shell portion 34c therebetween. Each of side shell portions 34a and 34b may be provided with padding material 39 facing the user's ankle. Padding 39 may be made of any suitable material, such as open cell foam, and in certain embodiments may be provided with an inflatable liner or airbags for supporting the user's ankle, such as that disclosed in U.S. Pat. No. 5,125,400, which is assigned to the assignee herein and which is incorporated by reference herein in its entirety. Side shell portions 34a and 34b can be coupled to center shell portion 34c, for example, by thermal welding, rivets, adhesive, or any other suitable fastening technique. Alternatively, side shell portions 34a and 34b and center shell portion 34c can be made as a contiguous single piece, for example, by injection molding.

Figure 12:
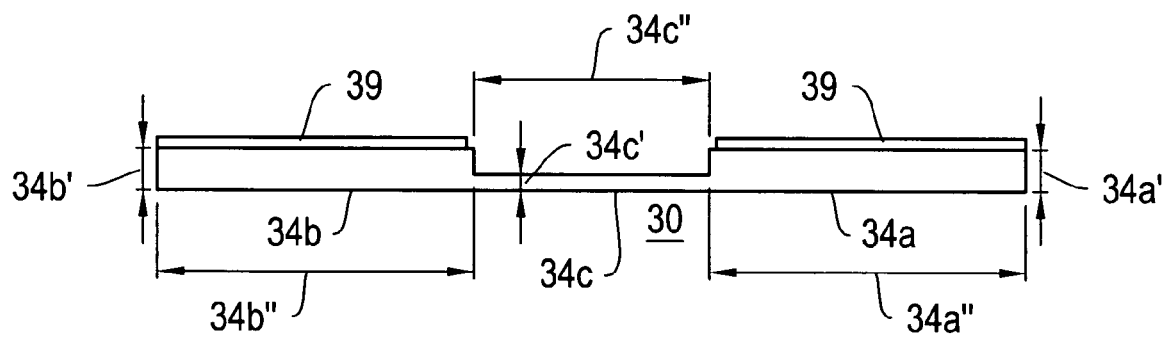
FIG. 12 is a side elevational view of the support shell of FIG. 11, taken from line 12-12 of FIG. 11.
Figure 13:
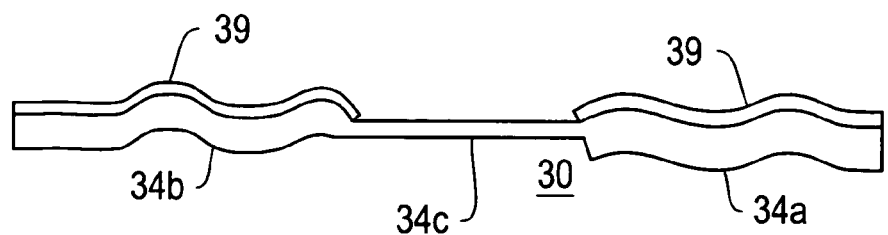
FIG. 13 is a side elevational view; similar to FIG. 12, of an alternative embodiment of a support shell according to the invention.

The length, thickness, shape, and stiffness of shell 30 can vary according to the materials employed and the application, as indicated schematically in FIGS. 12 and 13. In one embodiment, thickness 34c' of center shell portion 34c can range from between $\frac{1}{128}$" and $\frac{1}{32}$", and thicknesses 34a' and 34b' of side shell portions 34a and 34b, respectively, can each independently range from between $\frac{1}{8}$" and $\frac{1}{2}$", depending on the application of brace 10 and the size of the user, for example. Length 34c" of center shell portion 34c can range from between 2" and 6", and lengths 34a" and 34b" of side shell portions 34a and 34b, respectively, can each independently range from between 3" and 12", depending on the application of brace 10 and the size of the user, for example. As shown in FIG. 13, side shell portions 34a and 34b may be shaped so as to match the contours of a user's ankle and leg.

In one embodiment, as described above, shell 30 is inserted in a pocket 15 formed between structure 14 and assembly 12 (see, e.g., FIG. 3). Pocket 15 may extend from the top of brace 10 on the medial side, down under the forefoot, and up the lateral side to the top of the boot. As mentioned above and depicted in FIGS. 2, 3, and 10, side pocket portions 14a and 14b may be inclined rearward from the plane of the foot which contains axis 12' when wearing brace 10, for example, by an angle α. Angle α may be between 50° and 85°, and in certain embodiments is approximately 60° from the plane defined by the lower section of the boot that includes 12' when brace 10 is worn by the user.

An angle α of 60° has been found to be most effective to offer biomechanical support when the ankle is in the common position for spraining and most comfortable for the user and/or most effective in aiding the healing process following an injury. Side shell portions 34a and 34b may subtend the same angle α from its axis 30' as side pocket portions 14a and 14b do from axis 12' (see, e.g., FIG. 11). Shell 30 can fit within brace 10 (i.e., within pocket 15, as shown in FIG. 3, for example), such that the lateral and medial side shell portions 14a and 14b are collinear with the sides of the upper portion of the boot assembly 12, while axis 30' is collinear with axis 12', as shown in FIGS. 3-10, for example.

To increase comfort for the wearer of brace 10 and to prevent center shell portion 34c from pressing against the bottom of the user's forefoot when the shin is bent forward relative to the bottom of the forefoot, center shell portion 34c may be provided with a plurality of outwardly oriented fingers 36 that can individually flex, as shown in FIG. 11. In certain embodiments, shell 30 may be provided with four fingers 36, although any suitable number of fingers 36 may be used. In certain embodiments, the length 36' of fingers 36 may range from approximately half to double the uninterrupted width 34c''' of center shell portion 34c, and can each independently range from between ½" and 2", depending on the application of brace 10 and the size of the user, for example. It will be understood, however, that the dimensional aspects of center shell portion 34c and each of fingers 36 can be selected depending on the desired strength and pliability of center shell portion 34c.

FIGS. 9 and 10 show center shell portion 34c positioned under the user's forefoot, with fingers 36 pointing towards toes 2. When the user bends the foot forward (i.e., when the user plantarflexes his or her foot by moving leg 6 in the direction of arrow B of FIG. 10, such that his or her toes 2 flex downwards towards the sole in the direction of arrow C of FIG. 10), fingers 36 may flex, thereby reducing the pressure to the bottom of the forefoot that a conventional straight-cut center shell portion 34c without fingers 36 would otherwise apply in a direction opposite to the direction of arrow C. In certain embodiments, fingers 36 of center shell portion 34c are provided with enough flexibility such that they may yield to the movement of the user's foot while maintaining the stability and orientation of the lateral and medial supports with respect to the user's ankle (i.e., angle α).

The ankle brace described herein provides, among other things, prophylactic support to a user with, for example, a history of repeated ankle injuries. The brace includes a body and a shield both of which can slide over the user's foot and ankle. The brace is sufficiently thin to allow the user to fit a shoe and optionally a sock over the brace. The brace includes a shell with a relatively thin center section extending under the user's forefoot and having forwardly pointing fingers (i.e., towards the user's toes). This design ameliorates pressure applied to the bottom of the user's foot by conventionally constructed braces with a continuous wider center section.

Those skilled in the art will know or be able to ascertain using no more than routine experimentation, many equivalents to the embodiments and practices described herein. Accordingly, it will be understood that the invention is not to be limited to the embodiments disclosed herein, but is to be understood from the following claims, which are to be interpreted as broadly as allowed under the law.

What is claimed is:

1. A brace for supporting a user's ankle comprising:
 a boot assembly having:
  a medial side boot portion extending along a medial side of the user's ankle;
  a lateral side boot portion extending along a lateral side of the user's ankle;
  and a base boot portion connecting said side boot portions; and
 a shell having:
  at least one side support disposed in or on at least one of said medial and lateral side boot portions for providing support to at least one of the medial and lateral sides of the user's ankle, wherein the at least one side support is inserted in a pocket formed in or on said at least of said medial and lateral side boot portions; and
  a center shell portion coupled to said at least one side support and positioned under the user's forefoot and having a plurality of fingers oriented substantially towards the user's toes, wherein said fingers yield to movement of the user's forefoot.

2. The brace of claim 1, wherein said at least one side support being positioned at an angle between 50° and 80° in a rearward direction with reference to a ground support.

3. The brace of claim 2, wherein said angle is 60°.

4. The brace of claim 1, wherein said shell comprises a unitary piece.

5. The brace of claim 1, wherein said fingers yield to movement of the user's forefoot while the remainder of said center shell portion maintains the orientation of said at least one side support with respect to the user's ankle.

6. The brace of claim 1, wherein said shell comprises materials of different densities.

7. The brace of claim 1, wherein the material of said center shell portion has a greater flexibility than the material of said at least one side support.

8. The brace of claim 1, wherein a thickness of said at least one side support is greater than a thickness of said center shell portion.

9. The brace of claim 8, wherein said thickness of said at least one side support is non-uniform at different points on said brace.

10. The brace of claim 1, wherein said shell comprises plastic.

11. The brace of claim 1, wherein said shell comprises a material selected from the group consisting of polyethylene, polypropylene, metal, and composite.

12. The brace of claim 11 further comprising a padding layer disposed over an inner surface of said at least one side support.

13. The brace of claim 12, wherein said padding layer comprises at least one inflatable air cell for providing therapeutic pressure to at least one of the medial and lateral sides of the user's ankle.

14. The brace of claim 1, wherein said at least one side support being injection molded into said at least one of said medial and lateral side boot portions.

15. The brace of claim 1, wherein said base boot portion connects said side boot portions under the user's foot.

16. The brace of claim 1, wherein said boot assembly comprises a unitary piece.

17. The brace of claim 1, wherein said boot assembly further comprises a front boot portion extending along a front side of the user's leg and adapted to connect upper portions of said medial and lateral side boot portions for providing support to the front side of the user's leg.

18. The brace of claim 17, wherein said front boot portion connects said upper portions of said medial and lateral side boot portions with hooks and loops.

19. The brace of claim 17, wherein said front boot portion connects said upper portions of said medial and lateral side boot portions with lace apertures and laces.

20. The brace of claim 1, wherein said boot assembly comprises a material selected from the group consisting of nylon, neoprene, nylon-coated neoprene, cotton, plastic, foam, canvas, rubber, and spandex.

21. The brace of claim 1, wherein said boot assembly comprises a flexible material.

22. The brace of claim 1, wherein said boot assembly comprises a material that is selected from the group consisting of elastic material, non-elastic material, and a combination of elastic material and non-elastic material.

23. The brace of claim 1, wherein said boot assembly further comprises a strap extending from said medial side boot portion at a location proximal to the top of the user's forefoot, wherein said strap is adapted to be wound about and up said user's leg for holding said boot assembly in its desired firm supporting relationship with the user's ankle.

24. The brace of claim 1, wherein said boot assembly further comprises a vertical strap extending from said base boot portion at a location under the user's forefoot, wherein said vertical strap is adapted to be pulled up the medial side of the user's leg and foot for holding said boot assembly in its desired firm supporting relationship with the user's ankle.

25. A method of forming a brace for supporting a user's ankle comprising:
- forming a shell having at least one side support and having a center shell portion coupled to said at least one side support, said center shell portion having at least one finger capable of flexing in a direction perpendicular to a lengthwise direction of said shell;
- providing a flexible material having a pocket formed therein or thereon for retaining said shell;
- inserting said shell in said pocket and shaping said flexible material into a boot assembly, said at least one side supporting at least one of the medial and lateral sides of the user's ankle, said center shell portion being positioned under the user's forefoot and said at least one finger being oriented substantially towards the user's toes.

26. A method of claim 25, wherein the shell comprises materials of different densities.

27. A method of claim 25, wherein the material of said center shell portion has a greater flexibility than the material of said at least one side support.

28. A method of claim 25, wherein said boot assembly is comprised of a flexible material further comprising a strap extending from said medial side boot portion at a location proximal to the top of the user's forefoot, wherein said strap is adapted to be wound about and up said user's leg for holding said boot assembly in its desired firm supporting relationship with the user's ankle.

* * * * *